US00PP36561P2

(12) United States Plant Patent
Rimland

(10) Patent No.: US PP36,561 P2
(45) Date of Patent: Mar. 18, 2025

(54) ***MONSTERA* PLANT NAMED 'MKR-MTCM1'**

(50) Latin Name: *Monstera deliciosa*
Varietal Denomination: MKR-MTCM1

(71) Applicant: Costa Farms LLC, Miami, FL (US)

(72) Inventor: Michael Kerry Rimland, Miami, FL (US)

(73) Assignee: Costa Farms, LLC, Miami, FL (US)

( * ) Notice: Subject to any disclaimer, the term of this patent is extended or adjusted under 35 U.S.C. 154(b) by 0 days.

(21) Appl. No.: 18/831,281

(22) Filed: Oct. 11, 2024

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP35,706 P2 * 3/2024 Ployphommas ..... Plt./373

* cited by examiner

*Primary Examiner* — Karen M Redden
(74) *Attorney, Agent, or Firm* — Samuel R. McCoy, Jr.

(57) ABSTRACT

'MKR-MTCM1' is a new and distinctive *Monstera* plant which is characterized by a dwarfed growth habit with very small laminas, laminas that are moderately to strongly incised and fenestrated, dark green to yellow-green foliage that is irregularly blotched and flecked with a combination of light green and yellow-white, and the stability of all characteristics from generation to generation.

3 Drawing Sheets

Latin name of the genus and species: The Latin name of the genus and species of the novel variety disclosed herein is *Monstera deliciosa.*

Variety denomination: The inventive variety of *Monstera* disclosed herein has been given the variety denomination 'MKR-MTCM1'.

BACKGROUND OF THE INVENTION

Parentage: The claimed plant originated as a naturally occurring, whole-plant mutation of *Monstera deliciosa* 'Thai Constellation' (not patented). In June of 2024, the claimed plant was discovered by the inventor in a cultivated population of 'Thai Constellation' plants produced at plant nursery in Miami, Florida. Said plant was first noted for its significantly smaller size relative to all other plants in the population. From June of 2024 through September of 2024, the new plant was vegetatively propagated through three successive generations and the resulting plants grown to maturity in an effort to confirm the stability of the distinguishing characteristics first observed. In September of 2024, it was determined that the distinguishing characteristics of the claimed plant were indeed stable and that its diminutive size, in combination with the unique foliage variegation, would prove favorable for commercial marketability.

Asexual Reproduction: Asexual reproduction of 'MKR-MTCM1' in the form of rooting vegetative cuttings was first performed in June of 2024 at a wholesale plant nursery in Miami, Florida. Three successive generations so produced have shown that the unique features of the instant cultivar are stable and reproduced true to type.

SUMMARY OF THE INVENTION

The cultivar 'MKR-MTCM1' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Monstera* cultivar 'MKR-MTCM1'. These traits, in combination, distinguish 'MKR-MTCM1' as a new and distinct cultivar.

1. *Monstera* 'MKR-MTCM1' exhibits a dwarfed growth habit, growing to only about one-fourth the size of the parent; and
2. *Monstera* 'MKR-MTCM1' exhibits very small laminas with near-determinate growth rather than continuing to enlarge as plants age like the parent; and
3. *Monstera* 'MKR-MTCM1' exhibits laminas which are moderately to strongly incised and fenestrate; and
4. *Monstera* 'MKR-MTCM1' exhibits dark green to yellow-green foliage that is irregularly blotched and flecked with a combination of light green and yellow-white.

BRIEF DESCRIPTION OF THE FIGURES

The photographs were taken using conventional techniques and although colors may appear different from actual colors due to light reflectance it is as accurate as possible by conventional photographic techniques.

BOTANICAL DESCRIPTION OF THE PLANT

Figure 1:
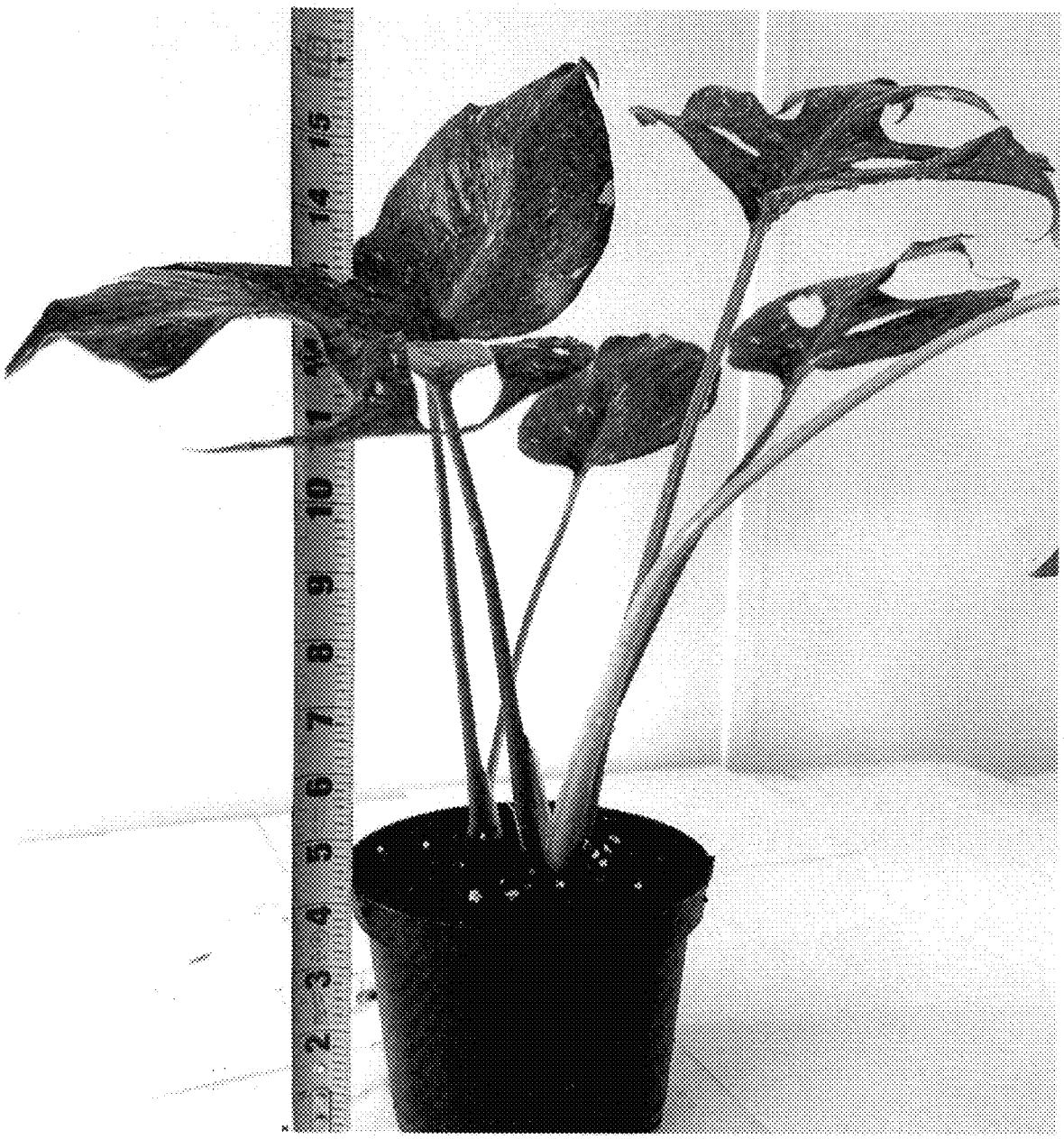
FIG. 1 illustrates an exemplary plant of the new cultivar, 'MKR-MTCM1'. The plant shown is approximately 9 months old from a rooted cutting, potted into a 15 cm nursery container, grown in a greenhouse in Miami, Florida.
Figure 2:
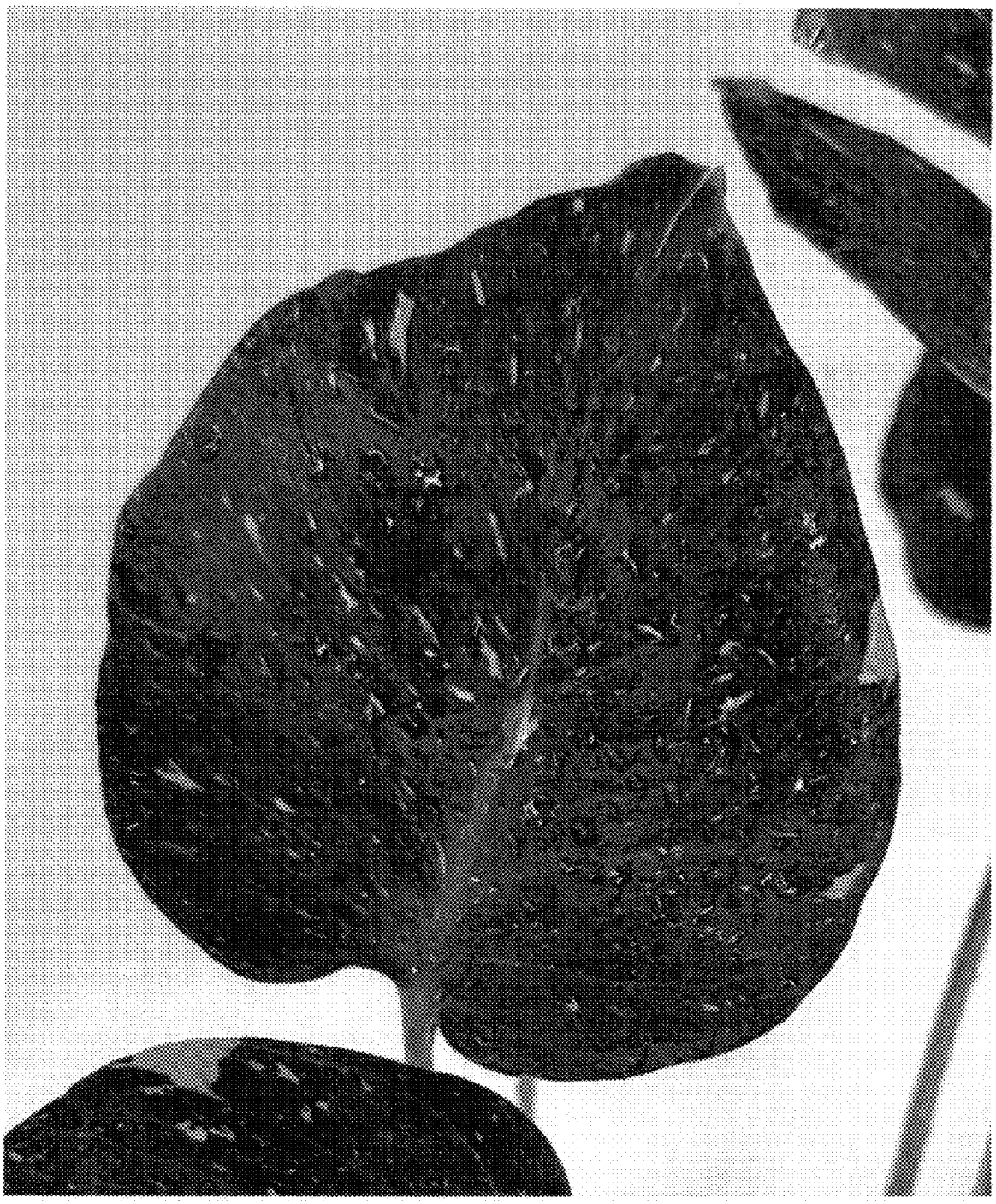
FIG. 2 illustrates the juvenile foliage of 'MKR-MTCM1'.
Figure 3:
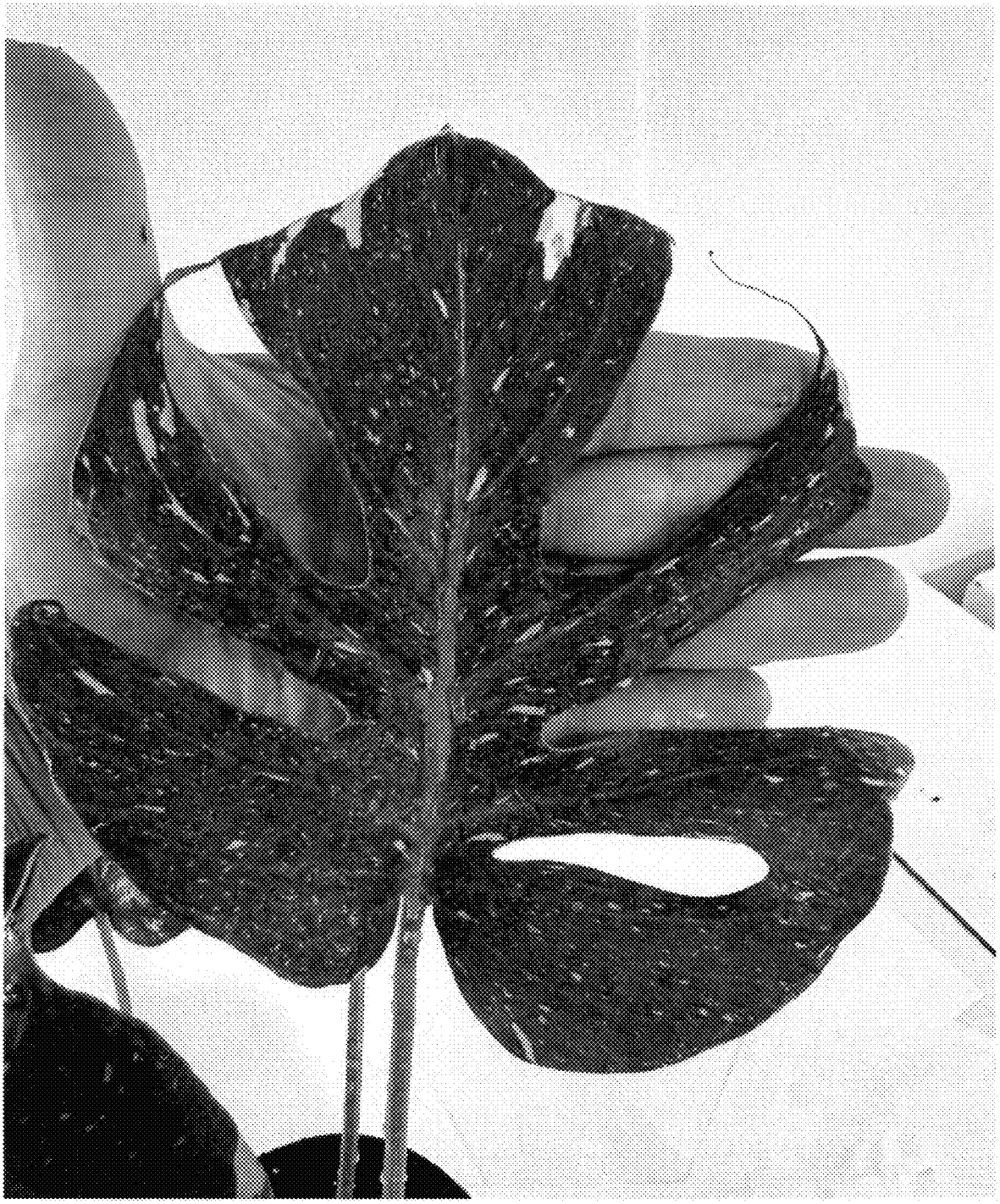
FIG. 3 illustrates the mature foliage of 'MKR-MTCM1'.

The following observations and measurements, made in October of 2024, describe a 9-month-old 'MKR-MTCM1' plant. The plant was grown from a single unrooted cutting, in 15 cm nursery containers, at a commercial greenhouse near Miami, Florida. The plant was produced using conventional greenhouse production protocols for *Monstera* sp. which entailed growing plants under 80 percent shade, regularly watering with overhead irrigation, and fertilizing with a 180-day slow-release granular fertilizer. No chemical pest measures or photoperiodic treatments were utilized during production.

Those skilled in the art will appreciate that certain characteristics will vary with older or, conversely, with younger plants. 'MKR-MTCM1' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on *The Royal Horticultural Society Colour Chart*, The Royal Horticultural Society, London, second edition.

A botanical description of 'MKR-MTCM1' and comparisons with the parent and the most similar variety of common knowledge are provided below.

General plant description:

*Growth habit*.—Monopodial evergreen perennial; plants will eventually develop a stem with age.

*Plant profile*.—Upright, globular.

*Height*.—Approximately 31.5 cm.

*Width*.—Approximately 38 cm.

*Plant vigor*.—Moderately vigorous.

*Propagation*.—Method — Vegetative stem cuttings. Time to initiate roots — Approximately 2 weeks to initiate roots at an average ambient temperature of 25 degrees Celsius. Crop time — Approximately 16 weeks to produce a well-rooted, marketable 15 cm container from a rooted cutting.

*Environmental tolerances*.—Moderately high tolerance to rain; low to moderate tolerance to wind; not drought tolerant; tolerant of temperatures to at least 35 degrees Celsius. Cold hardy to USDA Hardiness Zone 10.

*Pest resistance and susceptibility*.—Plants have not been observed to be any more or less susceptible or resistant to pathogens and pests common to *Monstera* sp.

Root system:

*General*.—*Monstera* sp. has the propensity to produce both subterranean and aerial roots.

*Branching*.—Freely branched.

*Density*.—Moderately dense.

*Distribution*.—Subterranean roots are shallow to moderately deep.

*Texture*.—Fleshy; smooth; aerial roots lack root hairs while subterranean roots are bare root hairs.

Stems:

*Branching characteristics*.—*Monstera* sp. is a monopodial plant; plants eventually develop a stem with age. However, to date, no stems have developed on the claimed plant.

Foliage:

*Arrangement*.—Spiraled.

*Division*.—Simple.

*Attachment*.—Petiolate.

*Quantity of leaves per shoot*.—4 to 5.

*Quantity of shoots per plant*.—2.

*Lamina*.—Shape — Cordate; laminas become progressively pinnatifid and fenestrated with age. Apex — Broadly acuminate. Base — Cordate. Aspect — Convex; laminar lobes are pendulous. Attitude — Laminas emerge in the same plane as the petiole yet mature to oblique or somewhat pendulous. Dimensions — 17.7 cm long and 15.6 cm wide. Margin — Juvenile foliar margins are entire with light, coarse undulation. Mature foliar margins are incised, lobed, and fenestrated, with coarse undulation. Texture and luster, adaxial surface — Smooth, glabrous, and lightly to moderately glossy. Texture and luster, abaxial surface — Smooth, glabrous, and slightly glossy to matte. Juvenile color, adaxial surface — Green, nearest to a mixture of RHS 137A and 137B, and lightly suffused with yellow-green, RHS 144A; irregularly flecked and blotched with a combination of light green, nearest to RHS 138D, and yellow-white, RHS 158D. Juvenile color, abaxial surface — Yellow-green, nearest to in between RHS 144B and 145A; irregularly flecked and blotched with a lighter shade of yellow-green, nearest to RHS 145C. Mature color, adaxial surface — Green, nearest to a mixture of RHS 137A and 137B, and lightly suffused with yellow-green, RHS 144A; irregularly flecked and blotched with a combination of light green, nearest to RHS 138D, and yellow-white, RHS 158D. Mature color, abaxial surface — Yellow-green, nearest to in between RHS 144B and 145A; irregularly flecked and blotched with a with a lighter shade of yellow-green, nearest to RHS 145C. Venation — Vein pattern — Pinnate. Vein color, adaxial surface — Yellow-green, nearest to RHS 144A. Vein color, abaxial surface — Yellow-green, nearest to RHS 145A.

*Petiole*.—Attachment — Sheathed. Aspect — Terete to subterete proximally and becoming semi-terete at the geniculum. Length — Approximately 24.5 cm. Width — Approximately 1.0 cm, including the petiole wings, at the proximal end, and 0.5 cm at the distal end. Strength — Moderately strong. Texture — Glabrous. Luster — Matte to very slightly glossy. Color of juvenile petioles, adaxial and abaxial surfaces — Yellow-green, nearest to in between RHS 147A and 144A. Color of mature petioles, adaxial surface — Yellow-green, RHS 144A, and lightly to moderately suffused with a lighter shade of yellow-green, nearest to RHS 145A; becoming progressively more suffused with RHS 145A at the geniculum. Color of mature petioles, abaxial surface — Yellow-green, RHS 145A, and lightly to moderately suffused with a darker shade of yellow-green, nearest to RHS 144A; becoming less suffused with RHS 144A at the geniculum. Geniculum — Length — 1.1 cm. Diameter — 0.6 cm. Aspect — Semi-terete, with genicular wings running along the length of the margins. Color, excluding genicular wings — Genicular wings — Dimensions — 1.0 cm long and 0.1 cm wide. Aspect — No undulation. Color — Yellow-green, RHS 145A. Texture and luster — Very slightly glossy. Color, adaxial surface — Yellow-green, RHS 145A. Color, abaxial surface — Yellow-green, RHS 145A. Petiole wings — General Description — Two petiole wings are present at the base of each petiole. Length — Approximately 9.2 cm. Width — Approximately 0.7 cm at the base. Margins — Entire; involute; lightly undulated. Texture and luster — Glabrous and very slightly glossy. Color, adaxial surface — Yellow-green, nearest to RHS 145A. Color, abaxial surface — Yellow-green, nearest to RHS 145A.

Inflorescence: *Monstera deliciosa* typically produces a spathe and spadix inflorescence, but no flowering of the claimed plant has been observed to date.

Flower buds: No flowering has been observed to date.

Flowers: No flowering has been observed to date.

Reproductive organs: No flowering has been observed to date.

Seed and fruit: Seed production has not been observed.

COMPARISONS WITH THE PARENT

Plants of the new cultivar 'MKR-MTCM1' may be distinguished from the parent, *Monstera deliciosa* 'Thai Constellation' (not patented), by the characteristics described in Table 1.

TABLE 1

| Characteristic | 'MKR-MTCM1' | 'Thai Constellation' |
|---|---|---|
| Size of the plant. | Significantly smaller than 'Thai Constellation'; approximately one-fourth of the size of 'Thai Constellation'. | Significantly larger than 'MKR-MTCM1'. |
| Size of the lamina. | Significantly smaller than 'Thai Constellation', with near-determinate growth. | Much larger than 'MKR-MTCM1', with indeterminate growth; laminas will continue to grow as the plant ages. |

COMPARISONS WITH THE MOST SIMILAR COMMERCIAL VARIETY

Plants of the new cultivar 'MKR-MTCM1' may be distinguished from the most similar commercial comparator known to the inventor, *Monstera deliciosa* 'Sumi1' (U.S. Plant Pat. No. 35,706), by the characteristics described in Table 2.

TABLE 2

| Characteristic | 'MKR-MTCM1' | 'Sumi1' |
|---|---|---|
| Lamina size. | Significantly smaller than 'Sumi1'; approximately one-half of the size of 'Sumi1'. | Larger than 'MKR-MTCM1', with indeterminate growth; laminas will continue to grow as the plant ages. |
| Petiole length, relative to plant height and lamina size. | Petioles are long relative to plant height and lamina size. | Petioles are short relative to the plant height and lamina size. |
| Petiole coloration. | Solid yellow-green, generally appearing as dark to mid green. | Green or green and white variegated. |
| Expression of the foliar color patterns; adaxial and abaxial surfaces. | Irregularly flecked and blotched with light green and pale yellow-white with cream white; blotches are less conspicuous than those of 'Sumi1'. | Irregularly flecked and blotched with a mixture of white, pale yellow-white, and pale orange-white; blotches are more conspicuous than those of 'MKR-MTCM1'. |

That which is claimed is:

1. A new and distinct variety of *Monstera deliciosa* plant named 'MKR-MTCM1', substantially as described and illustrated herein.

* * * * *